(12) United States Patent
Mullowney, Jr.

(10) Patent No.: US 6,516,676 B1
(45) Date of Patent: Feb. 11, 2003

(54) AIRBORNE EMISSIONS MONITORING PROBE

(76) Inventor: Robert Lee Mullowney, Jr., 2391 Bayview La., North Miami, FL (US) 33181

(*) Notice: Subject to any disclaimer, the term of this patent is extended or adjusted under 35 U.S.C. 154(b) by 0 days.

(21) Appl. No.: 09/537,350

(22) Filed: Mar. 29, 2000

(51) Int. Cl.$^7$ .................................................. G01N 1/00

(52) U.S. Cl. .................................................. 73/863.82

(58) Field of Search ..................... 73/861.01–861.03, 73/863.11, 863.82, 863.85, 863.73, 866.5; 374/148, 208

(56) References Cited

U.S. PATENT DOCUMENTS

| | | | | |
|---|---|---|---|---|
| 1,593,291 A | * | 7/1926 | Critchlow | .................. 73/866.5 |
| 3,888,123 A | * | 6/1975 | Kuntziger et al. | ....... 73/863.85 |
| 5,635,652 A | * | 6/1997 | Beaudin | .................. 73/863.03 |

* cited by examiner

*Primary Examiner*—Robert Raevis

(57) ABSTRACT

A probe to monitor airborne emissions contains all sensors and sampling tubes in one sleeve mounted at one location at the interior of a smokestack. Sensors include an airflow monitor and a temperature monitor. A separate blower tube us used to blow dirt off the sensors at the tip of the probe. Information received from the sensors and gas samples taken from within the smokestack are sent to a remote location for analysis. The probe is mounted on a bracket having three axes of rotation, thereby allowing the sensors and sampling tube to be located within the airstream at any desired position and orientation.

5 Claims, 3 Drawing Sheets

AIRBORNE EMISSIONS MONITORING PROBE

BACKGROUND OF THE INVENTION

As industrial development has increased on a worldwide scale, industrial emissions have become one of the most significant threats to the well-being of the world environment. In an attempt to limit, and even retard, the growth of such emissions, many industrialized countries have passed legislation requiring industries whose emissions are potentially harmful to the environment to take steps to monitor, control, and treat the amount and types of emissions that are released into the environment. Among the most harmful of the industrial wastes are airborne pollutants that may be caused by the burning of fossil fuel, or that may be the byproducts of other processes. Historically, the most common method of "treating" airborne pollutants has been to allow them to traverse up a smokestack, so that, when released into the atmosphere, they can be dispersed and diluted by the wind and will travel some distance before the heavier particulates return to earth.

A significant part of the United States Environmental Protection Agency's regulatory efforts are directed at fashioning methods for regulating and reducing noxious gaseous emissions. The first step in regulating gaseous emissions is to determine what substances, and how much of them, are being released through a smokestack or chimney. Traditionally, this task has been performed by using a series of probes that extend into the airflow in a smokestack and that measure air velocity, air temperature, air density, and other measurable parameters. Measurements of these parameters can then be accumulated and processed to provide such information as the chemical composition of various emissions and the amount that is being discharged at any given time.

The present invention is an improved probe in which all of the sensors needed to monitor and assess the amount and types of emissions that may be found within a flowing gaseous discharge are contained within a single device. The probe is suitable for use in a smokestack or other air flume through which a gaseous discharge may be directed. The probe is designed to sample the gases, temperature and flow rates of gas flowing through a smoke stack for the purpose of accurately reporting the pollution content as required by the US EPA under 40 C.F.R. part 75 of the Federal Register.

Traditional systems for obtaining this type of measurement have required at least two separate instruments installed in at least two separate mounting ports or holes in the inner surface of the smokestack. Accordingly, it is an object of this invention to incorporate all instruments needed to obtain gas content, flow rate, and temperature, within a single probe. It is a further object of this invention to provide a means to orient the probe and instruments contained therein in such a manner to obtain the most accurate measurements possible. It is yet another object of this invention to provide an internal means for cleaning the end of the probe so that physical removal and maintenance cleaning of the probe can be minimized or eliminated. It is a further object of this invention to provide signals and gas samples obtained by the probe to remotely-located computerized circuitry for analysis. These and other objects of the invention will become known through the following description of the invention.

SUMMARY OF THE INVENTION

The invention combines flow monitoring, temperature measurement, and gas sampling into a single probe. This solves the problem of requiring at least two ports and sometimes three or more ports in the smokestack. Multi ports are not desirable because they weaken the smokestack, and are expensive.

The invention also includes an improved system for orienting a probe within an airflow. Flow monitors require the ability to be positioned and rotated during setup in the field. This is because the accuracy of their measurements depends in large part upon locating the tip of the probe so as to obtain a smooth, laminar flow of gas across the flow monitor. Once a suitable location has been identified, the probe itself must be oriented such that the measuring instruments themselves do not create eddies that would affect the flow monitor. It is desirable for the flow monitor to be oriented such that air velocity is equal on either side of the probe, laterally, and the airstream across the measuring sensor is parallel to the airstream generally within the overall passageway. Where airflow across a flow monitor is variable or eddying, the maximum velocity recorded will not be indicative of the actual velocity of gas within the stack, and inaccuracies in calculated gas volumes and amounts of emissions will lead to errors in corrective measures. In contrast to flow monitors, gas sampling and temperature measurement instruments do not require such precise orientation. The problem of achieving the most desirable orientation is solved by a design that allows the flow measurement device to be rotated around the long axis of the probe and be rotated about its own long axis. The flow monitor is rotated until it reaches a null point, and then is rotated back 90 degrees to assure perfect attitude to the flue gas flow.

BRIEF DESCRIPTION OF THE DRAWINGS

Further objects and advantages of the present invention can be found in the detailed description of the preferred embodiment when taken in conjunction with the accompanying drawings in which.

DETAILED DESCRIPTION OF THE DRAWINGS

Figure 1:
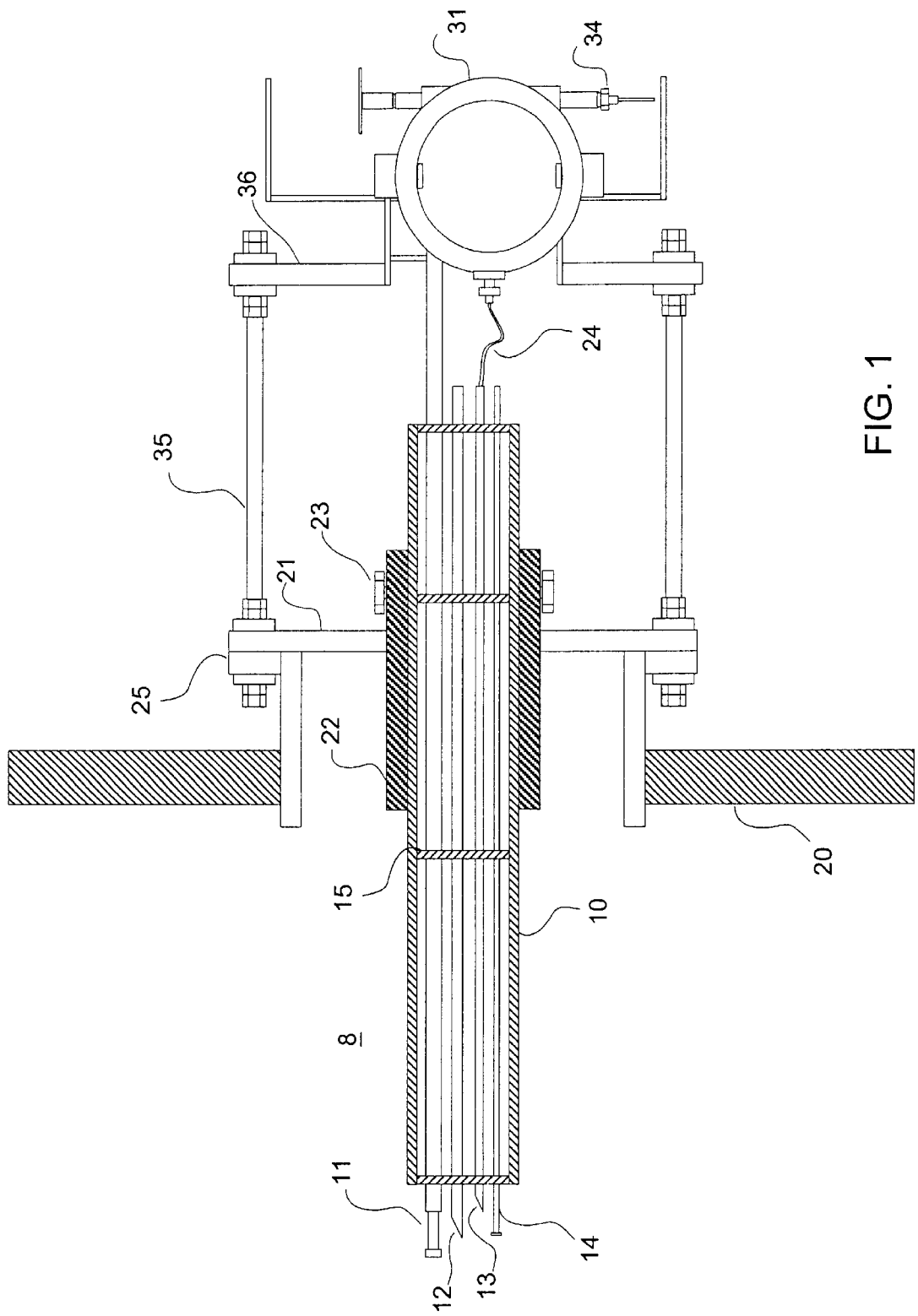
FIG. 1 depicts a partial cutaway elevation view of the probe with its multiple components installed within a sleeve. The sleeve is held within a probe bracket which is mounted to a mounting flange. Also attached to the mounting flange the transmitter box.

FIG. 1 is a view of the probe 8 and transmitter box 31. A rigid outer sleeve 10 protects the inner components of the probe while positioning them within a smokestack or air flume having a gaseous airflow. The sleeve is heavy wall pipe made of a material designed to withstand the gas conditions expected and to support its weight for the length of the probe and the temperature of the stack gases. The sleeve is of sufficient diameter to contain at least the tubes for an airflow monitor, a gas sampling tube, and a temperature measurement sensor. The sleeve is held within a probe bracket 22. Probe bracket 22 is affixed by welding or otherwise to mounting flange 21. The mounting flange and probe bracket are located in an alcove located a short distance back from the inner surface of the stack 20. By mounting the probe in a recessed alcove, airflow eddies that might otherwise influence measurements made at the end of the probe extending into the airstream are minimized. A setscrew 23 on the probe bracket permits rotational and longitudinal adjustment of the probe within the airstream to achieve a maximum of accuracy in measurements.

Within outer sleeve 10 is located a flow sensor 11, a gas sample probe 13, an air blower tube 12, and a thermocouple 14. These elements extend from the airstream through outer sleeve 10 back to a transmitter box 31 located in near proximity to the probe. Although the precise location of transmitter box 31 is not critical, it is important that it be located near the probe in order to minimize the distance that must be traveled by gas samples and electronic signals originating in the probe. Also within outer sleeve 10 are tube positioning spools or spacers 15 that maintain separation between the internal probe elements while holding them in position for making accurate measurements.

Signals from the airflow sensor 11, and the thermocouple 14, and gas samples from the gas sampling probe 13, sent through gas sampling line 24, are received at transmitter box 31, where they are retransmitted through a 5 conductor sensor cable and conduit 34 to a mass flow computer (not shown) for processing and analysis. An air blower line (not shown) connects the air blower tube 12 to a source of pressurized air (not shown). Periodically, pressurized air from air blower tube 12 is directed at the end of the flow sensor 11. This blast of air helps to keep dirt and other contaminants from forming on the tip of the flow sensor 11. The air may be supplied from an air pump or from a pressurized canister, and may, if desired, be dispensed together with a suitable cleaning solution.

As previously noted, setscrew 23 is used to orient the probe to minimize the affect of anomalies in the air flow across the end of the probe. To this effect, the setscrew and probe bracket 22 provide longitudinal and rotational movement for the probe about its longitudinal axis. By orienting the probe to minimize anomalous air flow, measurement accuracy may be maximized while measurement deviation is minimized.

Figure 2:
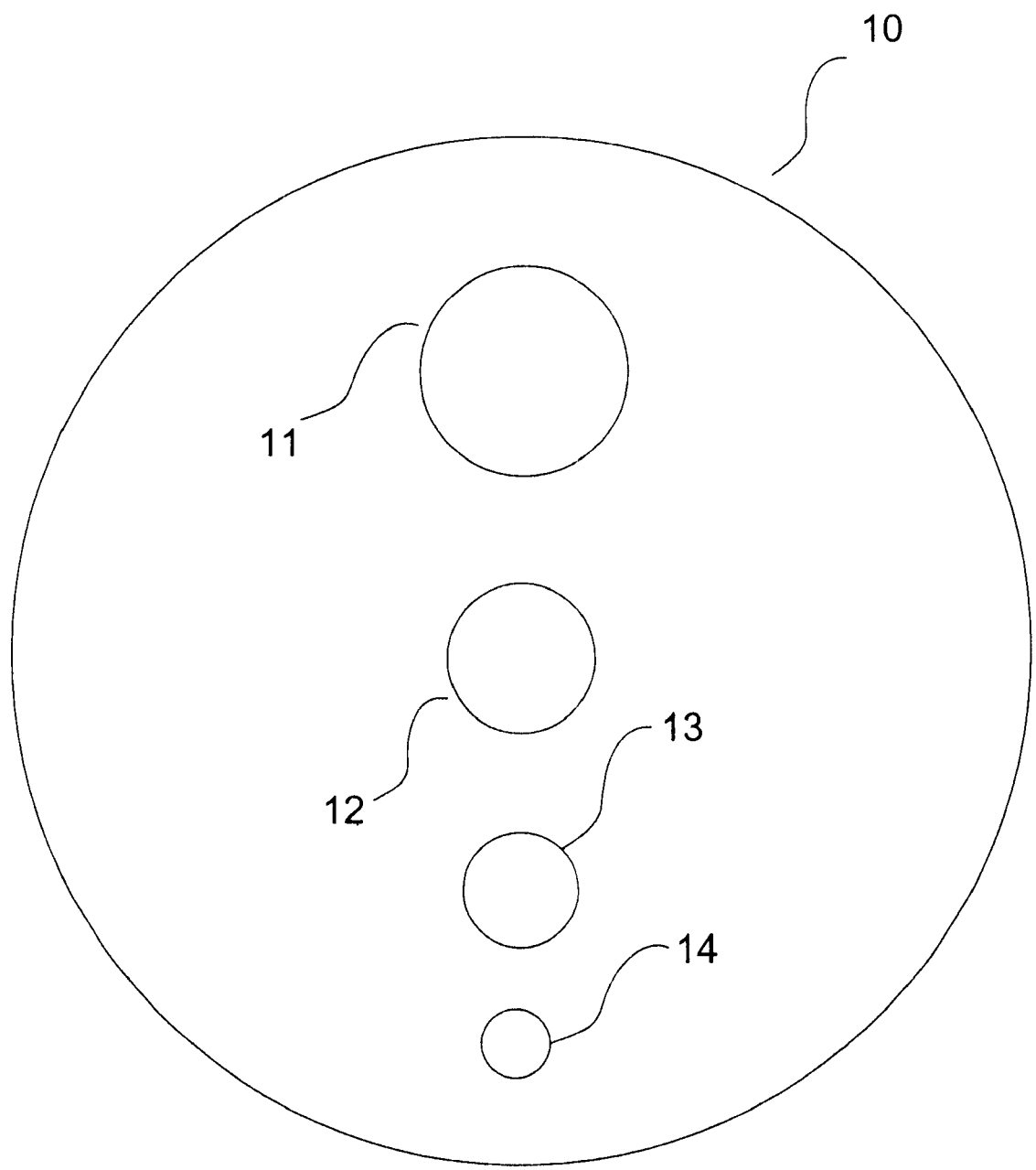
FIG. 2 shows the probe viewed from the end that protrudes toward the center of the smokestack.

As is shown in FIG. 2, a gas sampling probe 12, that can be heated or unheated as conditions require is at the center of the sleeve 10. At the outer edge of the sleeve is mounted the airflow sensor 11, which can be either a thermo or pitot tube type of flow measurement system. A thermocouple 14 for measuring temperature is mounted at the opposite side of the sleeve. The tubes are supported internally in the sleeve by support spools 15 placed strategically along the inside of the sleeve. The sleeve is heavy wall pipe made of a material designed to withstand the gas conditions expected and to support its weight for the length and temperature of the stack gases. The diameter of the sleeve is sufficient to contain the tubes of the airflow sensor, gas sampling and temperature measurement equipment. The entire assembly is designed to be withdrawn from the sleeve for repair or replacement.

The sleeve is supported in a probe bracket 22 and is held in place by setscrew 23. The probe bracket is welded to mounting flange 21 that is bolted to the smokestack. The mounting flange is attached to the transmitter box 31 by stand off bolts to allow room for adjustment of the airflow sensor. The resulting space is covered by a boot (not shown) to protect the exposed pipes.

Figure 3:
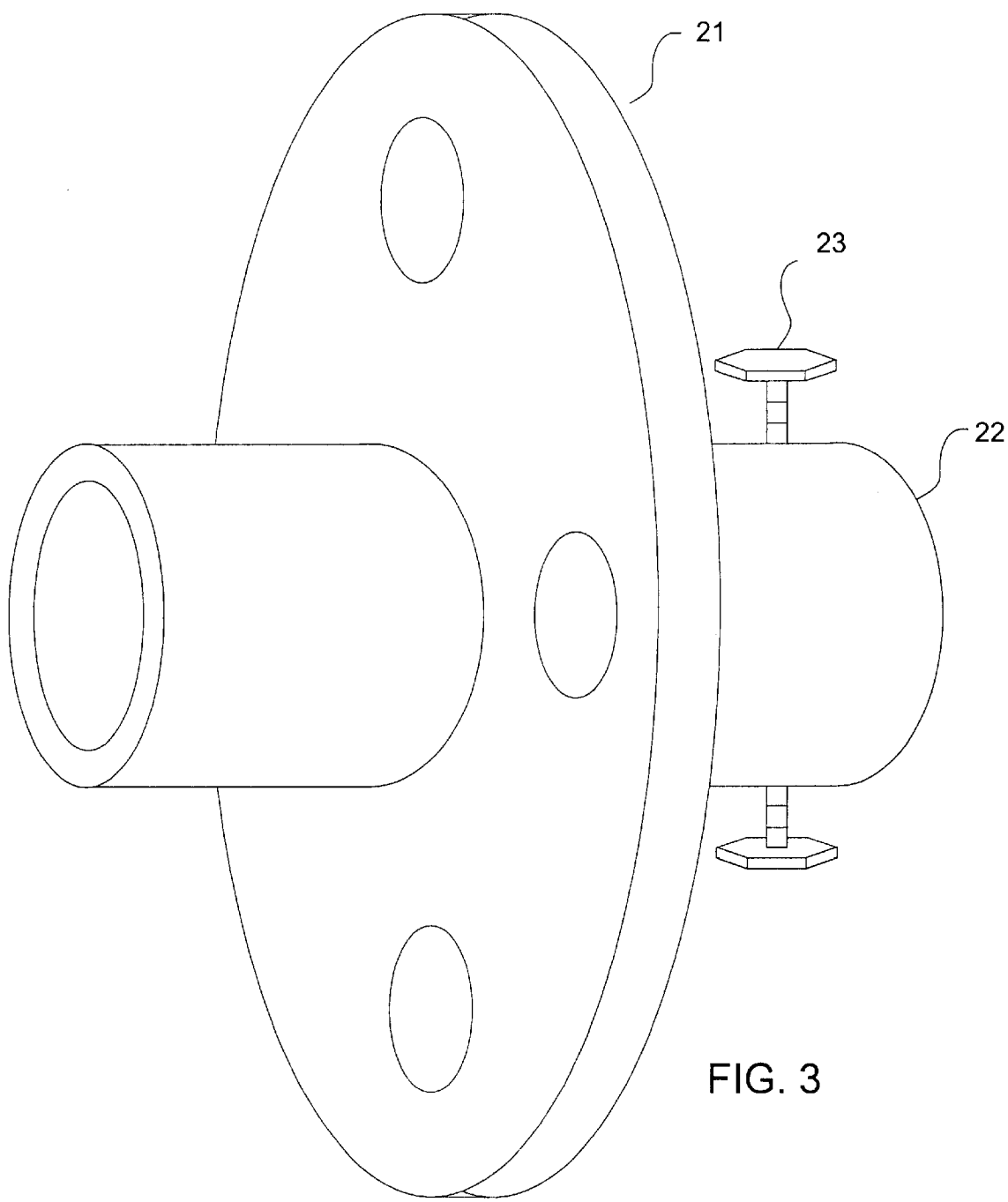
FIG. 3 shows a perspective view of the probe bracket.

As shown in FIG. 3, the probe bracket is attached to a flange 21 and has a bracket sleeve and a set screw 23 that may be tightened or loosened as necessary to permit movement of the probe within the probe bracket. When the set screw is loosened, the probe may be rotated within the probe bracket about its longitudinal axis, and may be moved longitudinally within the probe bracket to extend farther into the smokestack or to be withdrawn from the smokestack. Mounting flange 21 is attached to flange 25 with four bolts 35. Flange 25 is rigidly affixed to a structural component of the smokestack. Bolts 35 extend through flanges 25 and 21 to a flange 36 that supports the transmitter box 31. Flange 21 may be adjusted with respect to flange 25 by the use of shims placed between them. When mounted as shown, the probe bracket 22 may be adjusted and oriented by inserting shims of a proper size between the flanges 21 and 25. Such an arrangement permits some adjustment of the probe within the airstream.

It will be evident that the probe may include additional instruments and features without departing from the spirit of the invention described herein, and the addition of such additional features as may be needed to analyze an airstream is contemplated herein.

The claims appended hereto are meant to cover modifications and charges within the spirit and scope of the present invention.

What is claimed is:

1. A continuous emission monitoring probe for monitoring airborne emissions comprising:

a plurality of sensors for measuring physical characteristics of an airstream containing airborne emissions;

at least one of said sensors measuring the velocity of said airstream;

a second of said sensors measuring the temperature of said airstream;

each said sensor providing information regarding the said physical characteristic measured by said sensor to a remote location for processing;

each said sensor being held within an outer sleeve;

said outer sleeve being adjustably affixed to a probe bracket;

said probe bracket being located within a single mounting port in a surface adjacent said airstream and holding said outer sleeve and said sensors within said airstream;

said outer sleeve being adjustable and rotatable within said probe bracket and said mounting port such that said sensors can be positioned at a desired location within said airstream, and oriented with respect to said airstream.

2. A continuing emission monitoring probe as recited in claim 1, in which said single mounting port further comprises a port flange held rigidly with respect to said surface adjacent said airstream, said probe bracket being attached to a mounting flange, said mounting flange being adjustably attached to said port flange such that said outer sleeve is held within said probe bracket and can be adjusted to position and orient said probe within said airstream.

3. A continuing emission monitoring probe as recited in claim 1, further comprising an air sampling tube for extracting air samples from said airstream and delivering said samples to a remote location for analysis.

4. A continuing emission monitoring probe as recited in claim 3, further comprising an air cleaning system, said air cleaning system comprising an air blower tube and compressed air means whereby compressed air supplied by said compressed air means is directed through said air blower tube and is blown against said air velocity sensor causing airborne emission particles that have collected upon said air velocity sensor to become dislodged and carried away by said airstream.

5. An airborne emissions monitoring probe comprising a plurality of sensors for measuring the physical characteristics of air velocity and air temperature in an airstream carrying airborne emissions and delivering information regarding said physical characteristics to a remote location for analysis, a gas sampling tube for extracting samples of air containing airborne emissions from said airstream and delivering said samples to a remote location for analysis, and an air blower tube for blowing compressed air against said air velocity sensor, said sensors and said gas sampling tube being held within an outer sleeve that extends from a single mounting port into said airstream, said outer sleeve extending into said airstream and being adjustable to permit positioning of said sensors and said gas sampling tube to a desired location and orientation within said airstream.

* * * * *